(12) United States Patent
Park et al.

(10) Patent No.: US 12,303,276 B2
(45) Date of Patent: May 20, 2025

(54) WEARABLE DEVICE INCLUDING STRUCTURE FOR PREVENTING NOISE CAUSED BY STATIC ELECTRICITY

(71) Applicant: ATSENS CO., LTD., Gyeonggi-do (KR)

(72) Inventors: Soon Keun Park, Gyeonggi-do (KR); Jong Sung Kim, Seoul (KR); Seung Bum Cho, Gyeonggi-do (KR); Jong Ook Jeong, Gyeonggi-do (KR)

(73) Assignee: ATsens Co., Ltd., Gyeonggi-do (KR)

( * ) Notice: Subject to any disclaimer, the term of this patent is extended or adjusted under 35 U.S.C. 154(b) by 558 days.

(21) Appl. No.: 17/714,649

(22) Filed: Apr. 6, 2022

(65) Prior Publication Data

US 2023/0000414 A1 Jan. 5, 2023

(30) Foreign Application Priority Data

Jul. 5, 2021 (KR) .................. 10-2021-0087857

(51) Int. Cl.
*A61B 5/276* (2021.01)
*A61B 5/257* (2021.01)
(Continued)

(52) U.S. Cl.
CPC .............. *A61B 5/276* (2021.01); *A61B 5/257* (2021.01); *H05K 9/0086* (2013.01);
(Continued)

(58) Field of Classification Search
None
See application file for complete search history.

(56) References Cited

U.S. PATENT DOCUMENTS

| 8,483,809 B2 | 7/2013 | Kim et al. |
| 11,051,738 B2 | 7/2021 | Bahney et al. |

(Continued)

FOREIGN PATENT DOCUMENTS

| KR | 1020090102943 A | 10/2009 |
| KR | 1020150111970 A | 10/2015 |

(Continued)

OTHER PUBLICATIONS

Extended European Search Report of Counterpart EP Application No. 22167180.3 issued Sep. 22, 2022 (8 pages).

(Continued)

*Primary Examiner* — Linda C Dvorak
*Assistant Examiner* — Nicholas S Borsch
(74) *Attorney, Agent, or Firm* — Guntin & Gust, PLC; Miyoung Shin

(57) ABSTRACT

A wearable device is provided. The wearable device is used by being attached to a user's skin. The wearable device includes a main body unit having a housing and a substrate, the substrate being arranged inside the housing, an electrode unit including a sensing electrode connected to the main body unit, and a patch unit including one or more conductive members, the one or more conductive members being configured to electrically connect the electrode unit to the user's skin. The electrode unit includes a shielding layer that is not electrically connected to the main body unit. The shielding layer is conductive with a floating potential.

9 Claims, 7 Drawing Sheets

(51) Int. Cl.
*A61B 5/282* (2021.01)
*H05K 9/00* (2006.01)
(52) U.S. Cl.
CPC .... *H05K 9/0092* (2013.01); *A61B 2562/0209* (2013.01); *A61B 2562/04* (2013.01); *A61B 2562/166* (2013.01); *A61B 2562/182* (2013.01)

(56) References Cited

U.S. PATENT DOCUMENTS

| | | |
|---|---|---|
| 2010/0256474 A1 | 10/2010 | Faersnes et al. |
| 2015/0173639 A1* | 6/2015 | Ichida .................. A61N 1/0472 |
| | | 600/397 |
| 2016/0038074 A1* | 2/2016 | Brown .................. A61B 5/4848 |
| 2018/0368769 A1 | 12/2018 | Epstein |
| 2021/0102850 A1 | 4/2021 | Lim et al. |

FOREIGN PATENT DOCUMENTS

| | | |
|---|---|---|
| KR | 101784736 B1 | 10/2017 |
| KR | 1020180016847 A | 2/2018 |
| KR | 1020180061819 A | 6/2018 |
| KR | 1020200113819 A | 10/2020 |
| KR | 1020200113861 A | 10/2020 |

OTHER PUBLICATIONS

Office Action issued in Korean counterpart application No. 10-2021-0087857, issued Sep. 23, 2021, 5 pages.
Notice of Allowance issued in corresponding KR Application No. 10-2021-0087857, issued Jan. 27, 2022, 2 pages.

* cited by examiner

WEARABLE DEVICE INCLUDING STRUCTURE FOR PREVENTING NOISE CAUSED BY STATIC ELECTRICITY

CROSS-REFERENCE TO RELATED APPLICATION

This application is based on and claims priority under 35 U.S.C. § 119 to Korean Patent Application No. 10-2021-0087857, filed on Jul. 5, 2021, in the Korean Intellectual Property Office, the disclosure of which is incorporated by reference herein in its entirety.

BACKGROUND

1. Field

The disclosure relates to a wearable device, and more particularly, to a wearable device including a structure for preventing noise from deteriorating a measurement signal due to static electricity.

2. Description of the Related Art

A wearable device may be attached to a user's body, such as the user's abdomen, back, shoulder, or arm, to measure biosignals such as electromyography, electrocardiogram, blood pressure, or brain waves. For example, a wearable device for measuring an electrocardiogram, whose electrodes are in contact with the user's skin, detects electrical activity in the user's heart, and measures the electrocardiogram. Due to such characteristics, the wearable device should operate while being attached to the user's body for a long time.

Meanwhile, on dry days like in winter, static electricity is easily generated due to friction between clothes and the user's body. In particular, when the user does activities while the wearable device is attached to his or her body, static electricity is inevitably generated due to friction between clothes and the wearable device or the user's body. The generated static electricity generates noise in a measurement signal of the wearable device and thus deteriorates the measurement precision.

The above background art is technical information possessed by the inventor to derive the disclosure or obtained during a process of deriving the disclosure, and is not necessarily considered to be known art open to the general public prior to the filing of the disclosure.

SUMMARY

The disclosure has been devised to solve the above technical problem and provides a wearable device including a structure for preventing noise caused by static electricity. However, such a technical problem is an example, and the objective of disclosure to solve is not limited thereto.

Additional aspects will be set forth in part in the description which follows and, in part, will be apparent from the description, or may be learned by practice of the presented embodiments of the disclosure.

According to an embodiment of the disclosure, a wearable device, which is used by being attached to a user's skin, includes a main body unit including a housing and a substrate, the substrate being arranged inside the housing, an electrode unit including a sensing electrode connected to the main body unit, and a patch unit including one or more conductive members, the one or more conductive members being configured to electrically connect the electrode unit to the user's skin. The electrode unit includes a shielding layer not to be electrically connected to the main body unit, the shielding layer being conductive with a floating potential.

According to an embodiment of the disclosure, in the wearable device, the shielding layer may be arranged on an upper surface of the electrode unit to cover an electrode pattern layer printed on a rear surface of the electrode unit.

According to an embodiment of the disclosure, in the wearable device, the shielding layer may include a first shielding region and a second shielding region, the first shielding region being spaced apart from an edge of the main body unit by a certain distance, and the second shielding region extending from both sides of the first shielding region.

According to an embodiment of the disclosure, in the wearable device, when viewed from a top, a connection portion of the sensing electrode and the main body unit may be arranged inside the first shielding region, and the one or more conductive members may be arranged inside the second shielding region.

According to an embodiment of the disclosure, in the wearable device, the second shielding region may have a mesh structure therein.

According to an embodiment of the disclosure, in the wearable device, the shielding layer may be printed on an upper surface of the electrode unit with an inductive ink.

According to an embodiment of the disclosure, in the wearable device, a certain potential may be applied to the shielding layer so that external static electricity does not flow into the main body unit.

According to an embodiment of the disclosure, in the wearable device, the electrode unit may further include an electrode pattern layer that is printed on a rear surface of the electrode unit, is in contact with the user's skin through the one or more conductive members, and is connected to the shielding layer to cause external static electricity to flow into the user's skin.

According to an embodiment of the disclosure, a wearable device, which is used by being attached to a user's skin, includes: a main body unit including a housing and a substrate, the substrate being arranged inside the housing; an electrode unit including a sensing electrode connected to the main body unit; and a patch unit including one or more conductive members, the one or more conductive members being configured to electrically connect the electrode unit to the user's skin, wherein the electrode unit includes a conductive shielding layer including an electrode that is not electrically connected to the main body unit and is connected to the user's skin.

Other aspects, features, and advantages other than those described above will become apparent from the detailed description, claims and drawings for carrying out the following disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
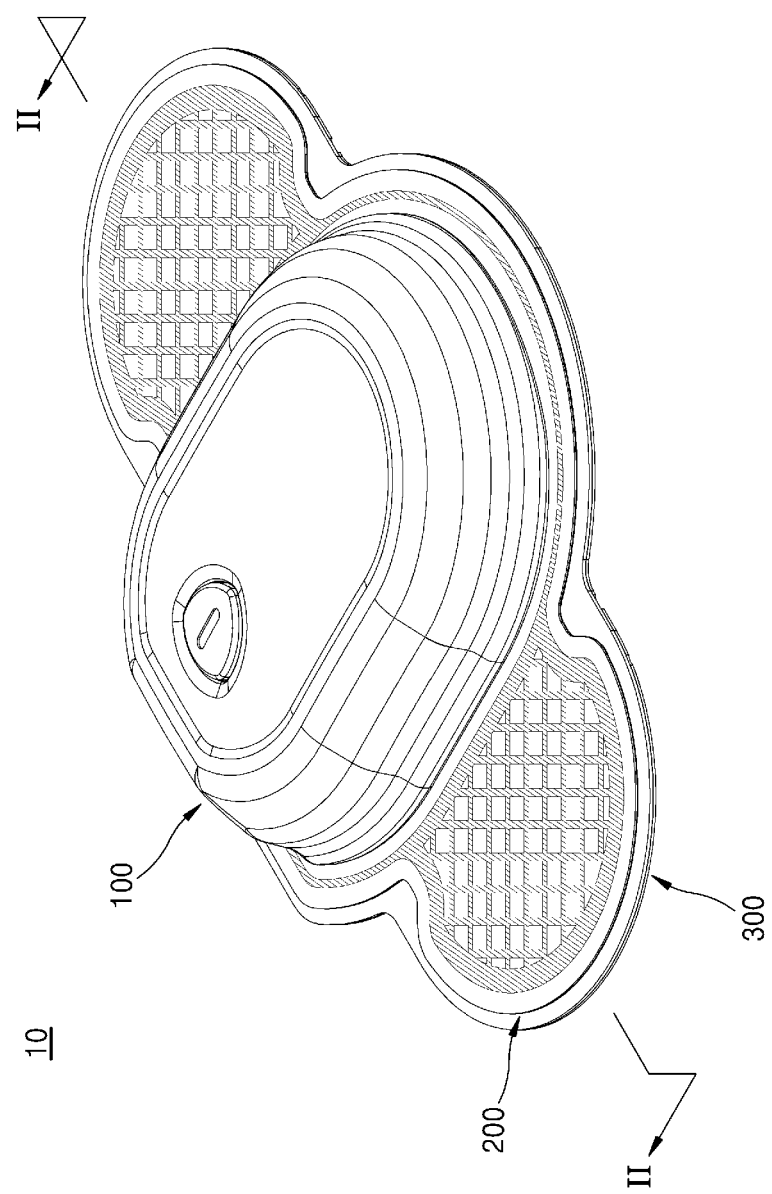
FIG. 1 illustrates a wearable device according to an embodiment of the disclosure.

Reference will now be made in detail to embodiments, examples of which are illustrated in the accompanying drawings, wherein like reference numerals refer to like elements throughout. In this regard, the embodiments of the present disclosure may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The disclosure may have various modifications and various embodiments, and specific embodiments are illustrated in the drawings and are described in detail in the detailed description. However, this is not intended to limit the disclosure to particular embodiments, and it will be understood that all changes, equivalents, and substitutes that do not depart from the spirit and technical scope of the disclosure are encompassed in the disclosure. In the description of the disclosure, even though elements are illustrated in other embodiments, like reference numerals are used to refer to like elements.

Hereinafter, embodiments of the disclosure will be described in detail with reference to the accompanying drawings, and in the following description with reference to the drawings, like reference numerals refer to like elements and redundant descriptions thereof will be omitted.

Although the terms "first," "second," etc. may be used to describe various elements, these elements should not be limited by these terms. These terms are only used to distinguish one element from another.

An expression used in the singular encompasses the expression of the plural, unless it has a clearly different meaning in the context.

It will be understood that the terms "comprise," "comprising," "include" and/or "including" as used herein specify the presence of stated features or elements but do not preclude the addition of one or more other features or elements.

Sizes of elements in the drawings may be exaggerated or reduced for convenience of explanation. In other words, because sizes and thicknesses of elements in the drawings are arbitrarily illustrated for convenience of explanation, the disclosure is not necessarily limited thereto.

The x-axis, the y-axis and the z-axis are not limited to three axes of the rectangular coordinate system, and may be interpreted in a broader sense. For example, the x axis, the y axis, and the z axis may be perpendicular to one another or may represent different directions that are not perpendicular to one another.

In the case where a certain embodiment may be implemented differently, a specific process order may be performed in the order different from the described order. As an example, two processes that are successively described may be substantially simultaneously performed or performed in the order opposite to the order described.

The terms used herein are only used to describe particular embodiments and are not intended to limit the scope of the disclosure. It will be understood that the terms "comprise," "comprising," "include" and/or "including" as used herein specify the presence of stated features, numbers, steps, operations, elements, parts, and combinations thereof, but do not preclude in advance the presence or addition of one or more other features, numbers, steps, operations, elements, parts, combinations thereof.

Figure 2:
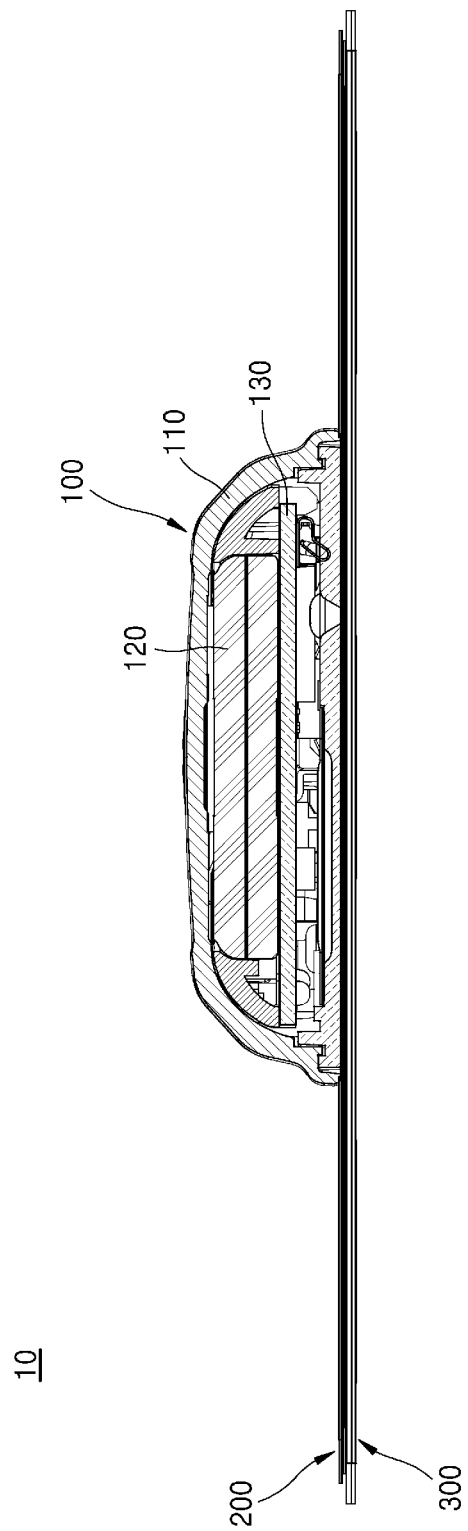
FIG. 2 illustrates a cross-section of the wearable device taken along a line II-II of FIG. 1.
Figure 3:
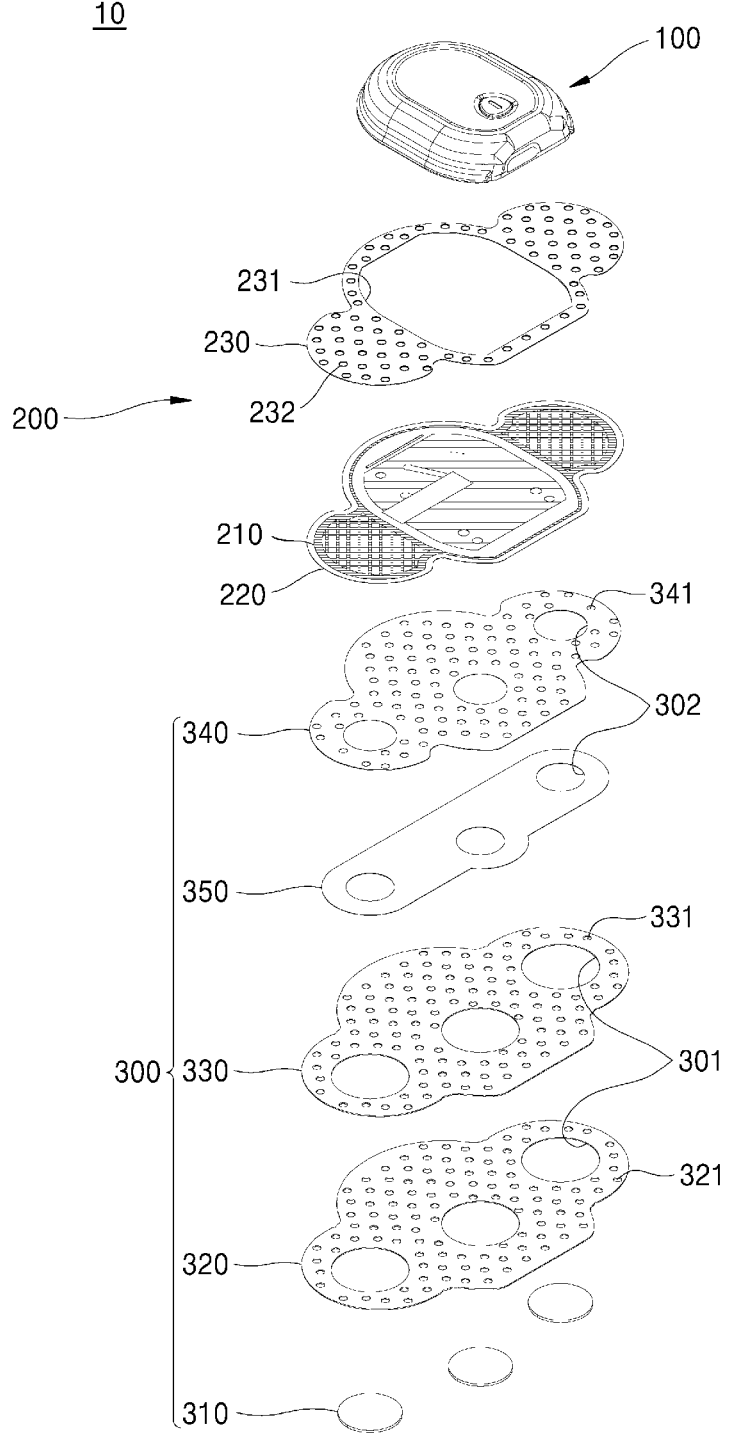
FIG. 3 is an exploded perspective view of a wearable device according to an embodiment of the disclosure.
Figure 4:
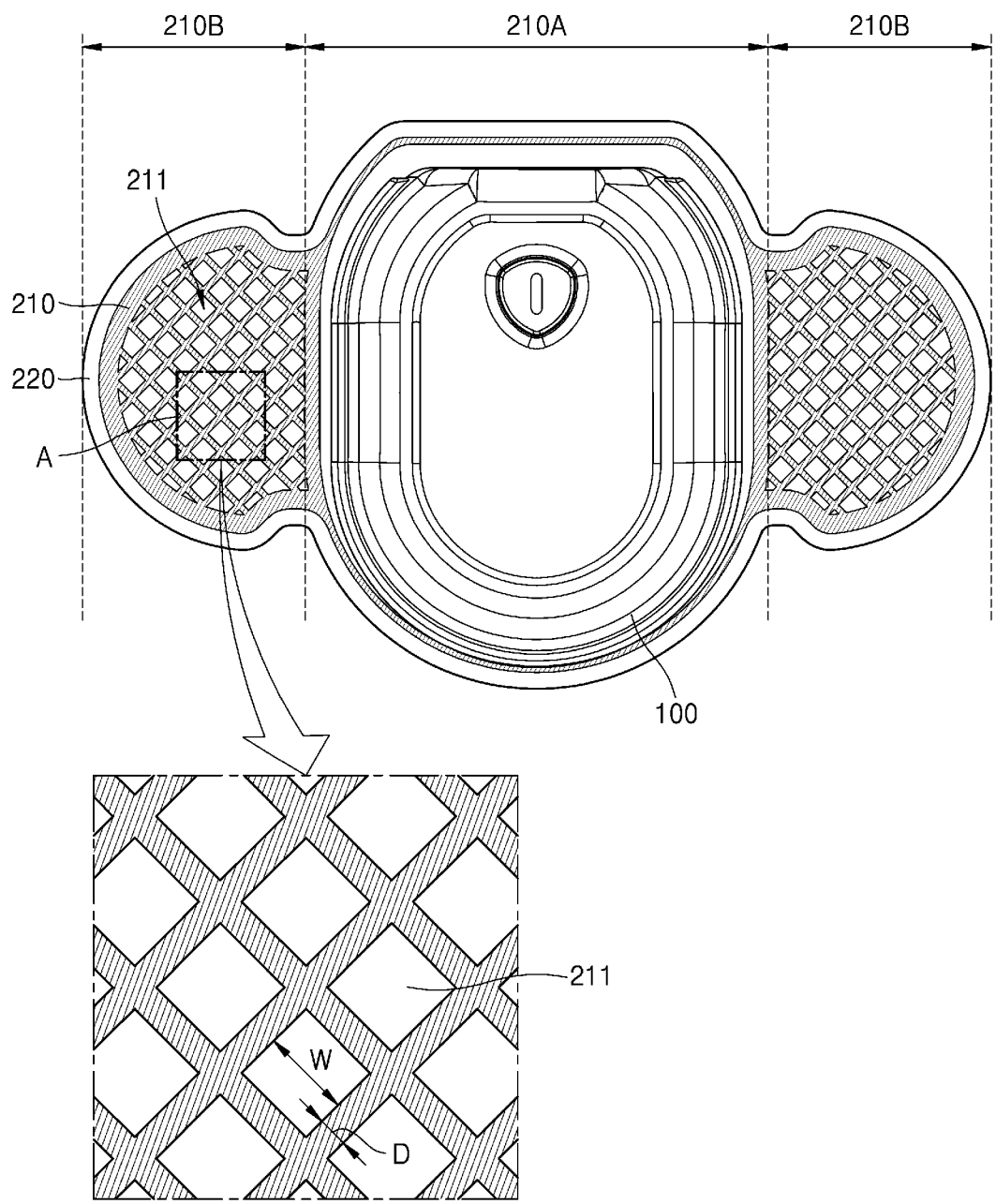
FIG. 4 is a top view of an electrode unit.
Figure 5:
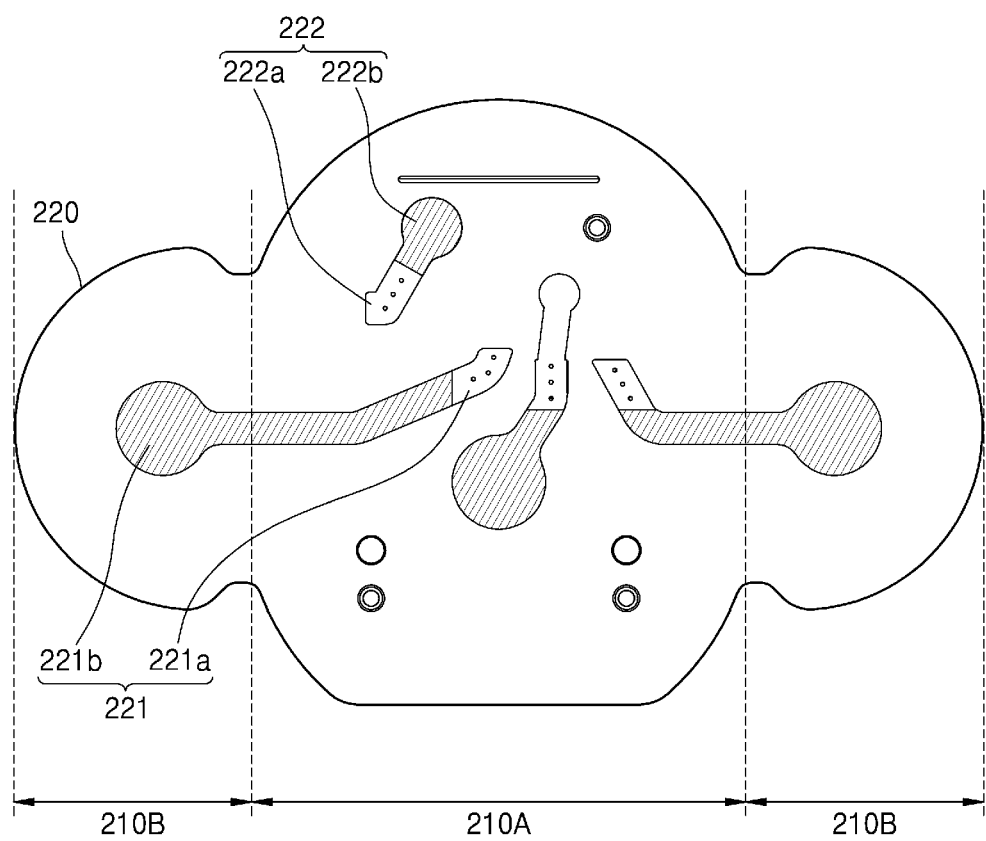
FIG. 5 illustrates an electrode pattern layer of an electrode unit.
Figure 6:
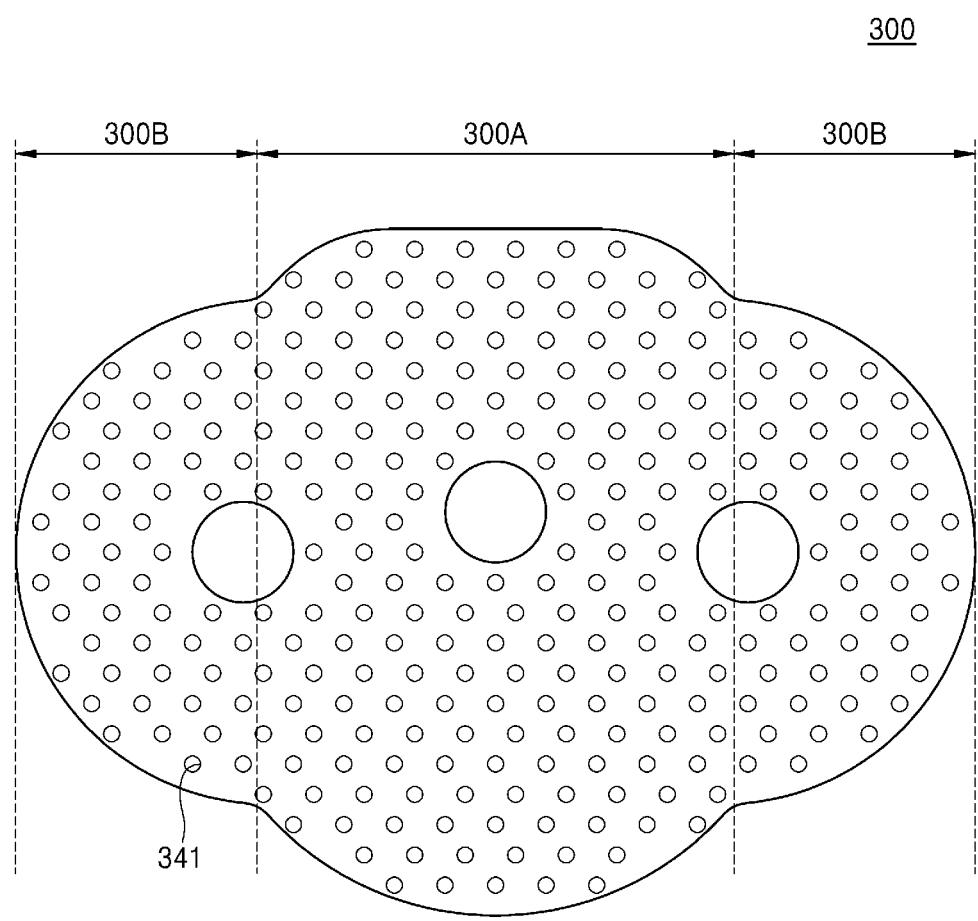
FIG. 6 is a top view of a patch unit.

FIG. 1 illustrates a wearable device 10 according to an embodiment of the disclosure, FIG. 2 illustrates a cross-section of the wearable device 10 taken along a line II-II of FIG. 1, FIG. 3 is an exploded perspective view of the wearable device 10, according to an embodiment of the disclosure, FIG. 4 is a top view of an electrode unit 200, FIG. 5 illustrates an electrode pattern layer 220 of an electrode unit, and FIG. 6 is a top view of a patch unit 300.

According to an embodiment of the disclosure, the wearable device 10 may be an electronic device that is used by being attached to a user's back, chest, shoulder, arm, or leg. For example, according to an embodiment of the disclosure, the wearable device 10 is attached to the user's skin and measures a biosignal such as an electrocardiogram (ECG), an electromyogram (EMG), or a blood pressure. In an embodiment, the wearable device 10 may be a device for measuring an ECG by inputting, by the electrode unit 200, a voltage generated along with a heartbeat. Alternatively, the wearable device 10 may be a device for measuring an electroencephalogram (EEG) by inputting, by the electrode unit 200, a voltage generated from cranial nerves. Alternatively, the wearable device 10 may be a device for measuring an EMG by inputting, by the electrode unit 200, a voltage generated from a skeletal muscle. Also, the wearable device 10 may be a continuous glucose monitor (CGM) or a transdermal therapeutic device using iontophoresis based on a measured biosignal such as an ECG, an EEG, or an EMG.

In an embodiment, the wearable device 10 may be in a contact switch type using a button or a touch switch type. The wearable device 10 may include a circuit for detecting the button press or detecting the touch of an object.

Referring to FIGS. 1 to 6, according to an embodiment of the disclosure, the wearable device 10 may include a main body unit 100, the electrode unit 200, and the patch unit 300.

The main body unit 100 is arranged on one side of the wearable device 10 and may include a housing 110, a battery 120, and a substrate 130. In addition, the main body unit 100 is a component for measuring an ECG while the wearable device 10 is attached to the user's body, and may include a processor, a memory, a display, an indicator, and other support structures. Hereinafter, specific components will be mainly described for convenience of description, but unless otherwise stated, components not described are not omitted or reduced in the wearable device 10.

The housing 110 protects other components of the main body unit 100 from an external shock and prevents an external foreign material from being introduced thereinto. A shape, a size, and a material of the housing 110 are not particularly limited and may be appropriately selected according to the purpose of use of the wearable device 10. In an embodiment, the housing 110 may have a dome shape including an internal space.

A button may be arranged on an upper surface of the housing 110. Although FIG. 1 illustrates that only one power button is arranged on the upper surface of the housing 110, the disclosure is not limited thereto. For example, a plurality of buttons for controlling power of the wearable device 10 and controlling an operation mode of the wearable device 10 may be arranged on the upper surface or a side surface of the housing 110.

The battery 120 and the substrate 130 may be arranged in the internal space of the housing 110. For example, as illustrated in FIG. 2, the substrate 130 may be supported by a support structure arranged in the internal space of the housing 110, and the battery 120 may be arranged on the substrate 130. Also, a signal amplification circuit for the wearable device 10 to operate, a signal processing circuit, a control circuit, a processor, and a memory may be arranged on the substrate 130.

In an embodiment, an antistatic paint may be coated on the inside of the main body unit 100. For example, an antistatic paint is coated or applied to the housing 110, so that external static electricity may be prevented from flowing into the main body unit 100 through the housing 110.

The electrode unit 200 may be arranged on one side of the main body unit 100 and may include a sensing electrode 221 (see FIG. 5) connected to the main body unit 100. For example, the electrode unit 200 may be connected to the substrate 130 of the main body unit 100, and the sensing electrode 221 may measure a potential appearing in relation to an electrogram on the body surface or apply a current to inject an electrolyte drug into the user's body through his or her skin or mucous membrane. Also, the sensing electrode 221 may measure an impedance between electrodes.

In an embodiment, the electrode unit 200 may include a shielding layer 210 and the electrode pattern layer 220.

The shielding layer 210 may include a conductive material such as a metal, and may be arranged on an upper surface of the electrode unit 200 to prevent an abnormal potential such as external static electricity from being applied to the sensing electrode 221 and affecting a measurement signal. In an embodiment, the shielding layer 210 may be arranged to cover the electrode pattern layer 220 printed on a rear surface of the electrode unit 200.

In an embodiment, the shielding layer 210 may include a first shielding region 210A and a second shielding region 210B. In more detail, as illustrated in FIGS. 3 and 4, the first shielding region 210A may be arranged at the center of the shielding layer 210 so that the main body unit 100 is arranged inside the first shielding region 210A. Also, when viewed from the top, the first shielding region 210A may be spaced apart from an edge of the main body unit 100 by a certain distance, and the main body unit 100 may be arranged inside the first shielding region 210A.

In an embodiment, when viewed from the top, a connection portion of the sensing electrode 221 and the main body unit 100 may be arranged inside the first shielding region 210A. That is, the first shielding region 210A may cover a first sensing electrode terminal 221a of the sensing electrode 221, which will be described below. Also, the first shielding region 210A may cover at least one of a plurality of conductive members 310.

The second shielding region 210B may extend from both sides of the first shielding region 210A. When viewed from the top, at least one conductive member 310 may be arranged inside the second shielding region 210B. That is, the second shielding region 210B may over at least one of the plurality of conductive members 310.

In an embodiment, the shielding layer 210 may be floating relative to the main body unit 100. That is, the shielding layer 210 and the main body unit 100 may maintain a state not electrically connected to each other and may have a floating potential. Accordingly, the influence of external static electricity on the main body unit 100 while flowing through the shielding layer 210 may be minimized.

In an embodiment, the shielding layer 210 may include a plurality of third ventilation holes 211 arranged in a certain pattern. For example, as illustrated in FIG. 4, when the shielding layer 210 is viewed from the top, the plurality of third ventilation holes 211 may be arranged on both sides of the shielding layer 210. That is, the third ventilation holes 211 may be arranged in the second shielding region 210B.

Accordingly, while the wearable device 10 is attached to the user's body, moisture generated from his or her skin may not flow into the main body unit 100 and may be discharged to the outside through the plurality of third ventilation holes 211.

In an embodiment, a width of a third ventilation hole 211 may be greater than a distance between adjacent third ventilation holes 211. In more detail, as illustrated in FIG. 4, a width W of the third ventilation hole 211 may be greater than a distance D between adjacent third ventilation holes 211.

Accordingly, the width of the third ventilation hole 211 may be sufficiently secured to increase moisture permeability, and static electricity applied from the outside may also flow to the outside through a ground electrode 222 of the electrode pattern layer 220, which will be described below, through a region between the third ventilation holes 211. Therefore, both the moisture permeability and an effect of preventing measurement noise caused by static electricity may be achieved.

Although FIG. 4 illustrates that the plurality of third ventilation holes 211 form a mesh structure, the disclosure is not limited thereto. For example, the plurality of third ventilation holes 211 may each have a circular shape, a polygonal shape, or a shape in which a straight line and a curved line are mixed, and may have different sizes and shapes.

In an embodiment, the shielding layer 210 may be printed on the upper surface of the electrode unit 200 with an inductive ink.

In an embodiment, the shielding layer 210 may be in a state in which a certain potential is applied through a separate circuit separated from the main body unit 100 to prevent external static electricity from flowing into the main body unit 100.

The electrode pattern layer 220 may be arranged on one surface of the electrode unit 200, for example, on the other surface of the electrode unit 200, which is a surface opposite to the shielding layer 210. For example, as illustrated in FIG. 5, the electrode pattern layer 220 may be printed on the rear surface of the electrode unit 200 and may include a plurality of sensing electrodes 221.

Although FIG. 5 illustrates that three sensing electrodes 221 are respectively arranged at the center and both sides of the electrode pattern layer 220 in a longitudinal direction, four or more sensing electrodes 221 or two or less sensing electrodes 221 may be present, and locations of the sensing electrodes 221 are not particularly limited. However, hereinafter, a case in which the wearable device 10 includes three sensing electrodes 221 will be mainly described for convenience of description.

Each of the sensing electrodes 221 may include a first sensing electrode terminal 221a connected to the main body unit 100 (in more detail, connected to the substrate 130 of the main body unit 100) and a second electrode terminal 221b connected to the conductive member 310 of the patch unit 300, which will be described below.

In an embodiment, the first sensing electrode terminal 221*a* of the sensing electrode 221 may be arranged at the center of the electrode pattern layer 220 in the longitudinal direction, and one second electrode terminal 221*b* may be arranged at each of the center and both sides of the electrode pattern layer 220.

In an embodiment, the electrode pattern layer 220 is in contact with the user's skin and is connected to the shielding layer 210, so that external static electricity may flow into the user's skin. In more detail, as illustrated in FIG. 5, the electrode pattern layer 220 may further include the ground electrode 222 in addition to the sensing electrodes 221. The ground electrode 222 may be in contact with the user's skin and may include a first ground electrode terminal 222*a* connected to the shielding layer 210 and a second ground electrode terminal 222*b* connected to the conductive member 310. Also, the ground electrode 222 may not be electrically connected to the main body unit 100 or the first ground electrode terminal 222*a* may be omitted.

As described above, the electrode pattern layer 220 is connected to the shielding layer 210 and the user's skin so that the user's skin may be used as a kind of ground. Accordingly, when static electricity is generated, energy of the static electricity transmitted from the shielding layer 210 may be grounded to the user's skin. Also, because the ground electrode 222 is not connected to the main body unit 100, external static electricity may be prevented from flowing into the main body unit 100.

The electrode unit 200 may further include an electrode protection layer 230. In addition to the shielding layer 210, the electrode protection layer 230 may block external static electricity to prevent static electricity from affecting the measurement precision of the wearable device 10. For example, as illustrated in FIG. 2, the electrode protection layer 230 may be arranged on the upper surface of the electrode unit 200, that is, on the shielding layer 210.

In an embodiment, the electrode unit 200 may include a conductor (e.g., a structure printed with a metal paint or a metal body), and a portion of the electrode unit 200 may not be electrically connected to the main body unit 100.

In an embodiment, the electrode protection layer 230 may have an area greater than those of other components of the electrode unit 200. In more detail, because the electrode protection layer 230 has an area greater than those of the shielding layer 210 and the electrode pattern layer 220, a portion of the wearable device 10 may be in contact with the user's body while the wearable device 10 is attached to the user's body.

Such a configuration may prevent external static electricity from affecting the main body unit 100 and cause static electricity to be applied to the user's body by using the user's body as a kind of ground electrode.

In an embodiment, the electrode protection layer 230 may include, on the inside thereof, a mounting groove 231 corresponding to a shape of the main body unit 100 and may include, on the outside thereof, a plurality of fourth ventilation holes 232 arranged in a certain pattern.

In more detail, as illustrated in FIGS. 1 and 2, when the electrode protection layer 230 includes the mounting groove 231 on the inside thereof and is arranged on the electrode unit 200, the main body unit 100 may be positioned inside the mounting groove 231. The mounting groove 231 may be positioned at the center of the electrode protection layer 230 in a longitudinal direction. Also, the plurality of fourth ventilation holes 232 may be arranged on both sides of the mounting groove 231, respectively.

In an embodiment, the plurality of fourth ventilation holes 232 may be arranged in the same pattern as the plurality of third ventilation holes 211. In this case, the same pattern means that sizes of a plurality of ventilation holes and distances therebetween may be slightly different from each other but shapes of the plurality of ventilation holes are the same as rectangular, square, rhombus, or circular shapes.

In an embodiment, the plurality of fourth ventilation holes 232 may be arranged to correspond to the plurality of third ventilation holes 211. That is, the plurality of fourth ventilation holes 232 may have the same size, shape, and location as the plurality of third ventilation holes 211. Also, the plurality of fourth ventilation holes 232 may have irregular shapes with permeability.

Accordingly, even though moisture is generated because the wearable device 10 is worn for a long time, moisture introduced into the electrode unit 200 through the patch unit 300 may be smoothly discharged to the outside through the third ventilation holes 211 and/or the fourth ventilation holes 232.

The patch unit 300 may be arranged under the electrode unit 200 and may be in direct contact with the user's skin to inject a drug into the user's skin.

In an embodiment, the patch unit 300 may include one or more conductive members 310 for electrically connecting the electrode unit 200 to the user's skin, and may include multiple layers including a plurality of ventilation holes.

In an embodiment, the patch unit 300 may include a main region 300A and a pair of sub-regions 300B extending from both sides of the main region 300A, respectively. For example, as illustrated in FIG. 6, the main region 300A may be arranged at the center of the patch unit 300 in a longitudinal direction, and the sub-regions 300B may be arranged on both sides of the main region 300A, respectively.

The conductive members 310 are members in direct contact with the user's skin while the wearable device 10 is attached to the user's skin, and may be electrically connected to the electrode unit 200. For example, each of the conductive members 310 may include a biocompatible material and may be hydrogel.

In an embodiment, the conductive members 310 may be in direct contact with the user's skin while being inserted into the patch unit 300 through mounting holes 301 provided in each of the main region 300A and the sub-regions 300B of the patch unit 300 by one. The mounting holes 301 may be formed through at least one of a plurality of layers of the patch unit 300 in a height direction. For example, the mounting holes 301 may be formed through a first attachment layer 320 and an absorption layer 330 of the patch unit 300, which will be described below. In addition, the conductive members 310 may be in contact with the electrode unit 200 while being inserted into the mounting holes 301.

In an embodiment, the conductive members 310 may be in contact with the electrode unit 200 while being inserted into the patch unit 300 through contact holes 302 provided in each of the main region 300A and the sub-regions 300B of the patch unit 300 by one. The contact holes 302 may be formed through at least one of the plurality of layers of the patch unit 300 in the height direction. For example, the contact holes 302 may be formed through a second attachment layer 340 and a current-stopping layer 350 of the patch unit 300, which will be described below. In addition, the conductive members 310 may be in contact with the electrode unit 200 through the contact holes 302 while being inserted into the mounting holes 301.

In an embodiment, ventilation holes of the patch unit 300 may be arranged in at least one of the main region 300A and the sub-regions 300B except for a region in which the mounting holes 301 and/or the contact holes 302 are formed.

In an embodiment, the patch unit 300 may include the first attachment layer 320, the absorption layer 330, the second attachment layer 340, and the current-stopping layer 350.

The first attachment layer 320 is a member in direct contact with the user's skin and may be an adhesive member for fixing the patch unit 300 to the user's skin. For example, the first attachment layer 320 is a tape including a biocompatible material and may be a silicon tape.

In an embodiment, the first attachment layer 320 may include a plurality of first ventilation holes 321. For example, as illustrated in FIG. 3, the first ventilation holes 321 may be randomly arranged on the entire surface of the first attachment layer 320 in a remaining region except for the mounting holes 301. Accordingly, sweat generated on the user's skin may be discharged to the outside through the first attachment layer 320 without staying in the first attachment layer 320 for a long time.

The absorption layer 330 may be arranged on the first attachment layer 320 and may include a material capable of retaining moisture so that the sweat generated on the user's skin or external moisture does not flow into the main body unit 100 or the electrode unit 200. In an embodiment, the absorption layer 330 may be a fibrous layer, and more particularly, may include a non-woven fabric and may re-discharge retained moisture.

The second attachment layer 340 is a member for attaching the patch unit 300 to the electrode unit 200, may be arranged on the absorption layer 330 to connect the electrode unit 200 to the patch unit 300, and may include a plurality of second ventilation holes 341. An adhesive material may be coated on both sides of the second attachment layer 340, and the second attachment layer 340 may be a double-sided tape.

In an embodiment, the plurality of second ventilation holes 341 may be arranged to communicate with the plurality of first ventilation holes 321 in a height direction. That is, the plurality of second ventilation holes 341 may be arranged at positions corresponding to the plurality of first ventilation holes 321. Alternatively, the plurality of second ventilation holes 341 may be arranged in the same pattern as the plurality of first ventilation holes 321. Alternatively, the plurality of second ventilation holes 341 may be arranged with the same size, shape, and number as the plurality of first ventilation holes 321.

The patch unit 300 may further include current-stopping layer 350.

As illustrated in FIG. 3, the current-stopping layer 350 may be between the absorption layer 330 and the second attachment layer 340 and may prevent current flowing between other members of the wearable device 10 or prevent fine current application between the wearable device 10 and the user's skin.

In an embodiment, the current-stopping layer 350 may include a moisture-permeable material and may be a moisture-permeable polyurethane tape.

In an embodiment, the current-stopping layer 350 may also include ventilation holes, and the ventilation holes may be arranged to communicate with ventilation holes of the first attachment layer 320, the absorption layer 330, and the second attachment layer 340. For example, the ventilation holes of the current-stopping layer 350 may be arranged with the same number, pattern, and shape as the ventilation holes of the first attachment layer 320, the absorption layer 330, and the second attachment layer 340. Although it has been described that the patch unit 300 includes a plurality of layers, the patch unit 300 may be simplified by using the same function or different materials.

Figure 7:
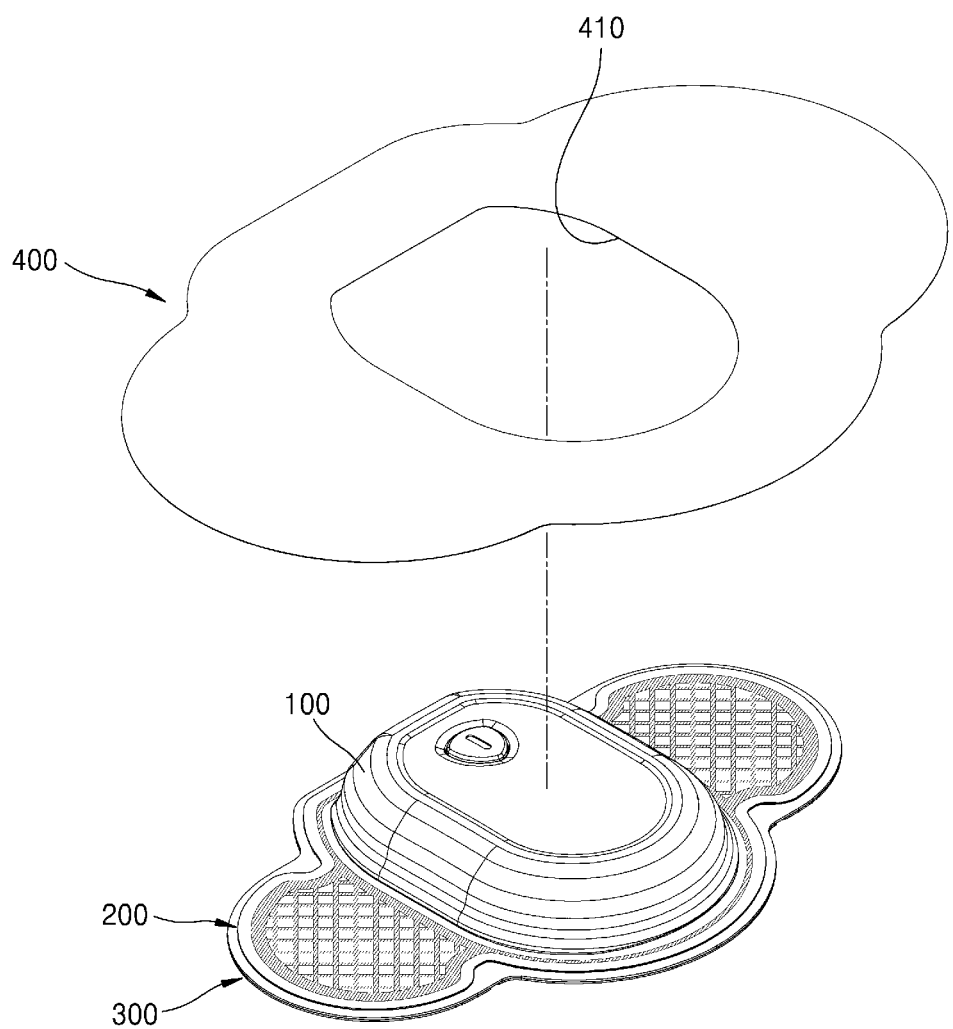
FIG. 7 illustrates a wearable device according to another embodiment of the disclosure.

FIG. 7 illustrates a wearable device 10A according to another embodiment of the disclosure.

According to the present embodiment, the wearable device 10A may further include a fixing unit 400.

The fixing unit 400 includes an accommodation groove 410 in which the main body unit 100 is accommodated, and both side regions of the accommodation groove 410 covers the upper surface of the electrode unit 200.

In an embodiment, the fixing unit 400 may have an area greater than those of the electrode unit 200 and/or the patch unit 300. In more detail, as illustrated in FIG. 7, at least a portion of the fixing unit 400 may protrude to the outside of the electrode unit 200 and/or the patch unit 300 to adhere to the user's skin while the fixing unit 400 is arranged on the electrode unit 200.

In an embodiment, the fixing unit 400 may include a moisture-permeable material. For example, the fixing unit 400 may include a material having moisture directionality, such as a moisture-permeable polyurethane tape or Gore-Tex. Also, the fixing unit 400 may include a waterproof material. Accordingly, the fixing unit 400 may prevent external moisture from flowing into the inside of the wearable device 10A (waterproofness) and may discharge internal moisture to the outside (moisture permeability).

Hereinafter, a method of manufacturing a wearable device, according to an embodiment of the disclosure, will be described.

According to an embodiment of the disclosure, the method of manufacturing the wearable device may manufacture a wearable device 10 used by being attached to a user's skin, by assembling a patch unit 300 by stacking a plurality of layers, and stacking the assembled patch unit 300, an electrode unit 200, and a main body unit 100. Also, according to an embodiment of the disclosure, the method of manufacturing the wearable device may form a plurality of ventilation holes in the patch unit 300 by blanking the plurality of stacked layers by using a press tool.

First, the patch unit 300 is assembled by stacking the plurality of layers. For example, the patch unit 300 is assembled by stacking a first attachment layer 320, an absorption layer 330, a second attachment layer 340, and a current-stopping layer 350.

Next, the electrode unit 200 is assembled by assembling and stacking a plurality of members in a similar manner. For example, the electrode unit 200 may be assembled by forming a shielding layer 210 and an electrode pattern layer 220 in the electrode unit 200, and then arranging an electrode protection layer 230 on the shielding layer 210. However, an order of assembling the electrode unit 200 and the patch unit 300 is not particularly limited, and the electrode unit 200 may be assembled first or the electrode unit 200 and the patch unit 300 may be assembled simultaneously.

Next, ventilation holes are formed in the patch unit 300 by performing a blanking process by using the press tool. For example, the plurality of ventilation holes may be formed in the patch unit 300 by blanking the patch unit 300, in which the plurality of layers, such as the first attachment layer 320, the absorption layer 330, the second attachment layer 340, and the current-stopping layer 350, are stacked, by using the press tool.

Next, the wearable device 10 is manufactured by stacking the blanked patch unit 300, the electrode unit 200, and the main body unit 100.

In an embodiment, before the electrode unit 200 is assembled, ventilation holes are formed by blanking the shielding layer 210 and the electrode protection layer 230 by using the press tool, and then, the electrode unit 200 may be assembled. In this case, the shielding layer 210 and the electrode protection layer 230 may be blanked while the shielding layer 210 and the electrode protection layer 230 are stacked, or the shielding layer 210 and the electrode protection layer 230 may be blanked separately.

In another embodiment, when ventilation holes having different shapes and patterns are to be formed in the plurality of layers of the patch unit 300, a blanking process may be performed on each member first before the patch unit 300 is stacked. That is, a blanking process may be performed by using different press tools for each of the first attachment layer 320, the absorption layer 330, the second attachment layer 340, and the current-stopping layer 350 of the patch unit 300. Next, the patch unit 300 may be assembled by stacking the first attachment layer 320, the absorption layer 330, the second attachment layer 340, and the current-stopping layer 350.

According to an embodiment of the disclosure, the wearable device has a structure for preventing noise caused by static electricity, the structure preventing external static electricity from affecting a main body unit, and thus, the measurement precision of the wearable device may be prevented from deteriorating due to external static electricity.

As described above, the disclosure has been described with reference to the embodiment illustrated in the drawings, but this is merely an example. Those of ordinary skill in the art will fully understand that various modifications and other equivalent embodiments can be made from the embodiments. Therefore, the scope of the protection of the technology of the disclosure should be determined by the appended claims.

Specific technical descriptions in the embodiments are embodiments and do not limit the technical scope of the embodiments. In order to concisely and clearly describe the disclosure, descriptions of general techniques and configurations of the related art may be omitted. Also, connections or connection members of lines between elements illustrated in the drawings are examples of functional connections and/or physical or circuit connections, and may be represented by various alternative or additional functional connections, physical connections, or circuit connections in an actual device. In addition, unless specifically stated as "essential" or "importantly", an element may not be a necessary element for the application of the disclosure.

The term "above" or similar referring expressions used in the description and claims of the disclosure may refer to both the singular and plural expressions unless otherwise specified. Also, when a range is described in the embodiments, it means that embodiments to which individual values belonging to the range are applied are also included (unless otherwise stated), it is the same as each individual value constituting the range is described in the detailed description of the disclosure. Moreover, steps or operations constituting the method according to the embodiments may be performed in an appropriate order, if the order is explicitly stated or unless otherwise stated. The embodiments are not necessarily limited according to the order of the description of the steps or operations. All examples or illustrative terms (e.g., etc.) in the embodiments are merely used to describe the embodiments in detail, and the scope of the embodiments is limited by the examples or illustrative terms unless limited by the claims. In addition, those of ordinary skill in the art will appreciate that various modifications, combinations, and changes can be made in accordance with design conditions and factors within the scope of the appended claims or equivalents thereof.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope included in the following claims.

What is claimed is:

1. A wearable device used by being attached to a user's skin, the wearable device comprising:
    a main body unit including a housing and a substrate, the substrate being arranged inside the housing;
    an electrode unit including a sensing electrode connected to the main body unit; and
    a patch unit including one or more conductive members, the one or more conductive members being configured to electrically connect the electrode unit to a user's skin,
    wherein the electrode unit further includes a shielding layer, the shielding layer configured to be not electrically connected to the main body unit and to be conductive with a floating potential.

2. The wearable device of claim 1, wherein the shielding layer is on an upper surface of the electrode unit to cover an electrode pattern layer printed on a rear surface of the electrode unit.

3. The wearable device of claim 2, wherein the shielding layer includes a first shielding region and a second shielding region, the first shielding region being spaced apart from an edge of the main body unit by a predetermined distance, and the second shielding region extending from both sides of the first shielding region.

4. The wearable device of claim 3, wherein, when viewed from a top, a connection portion of the sensing electrode and the main body unit is arranged inside the first shielding region, and the one or more conductive members are arranged inside the second shielding region.

5. The wearable device of claim 3, wherein the second shielding region includes a mesh structure therein.

6. The wearable device of claim 1, wherein the shielding layer is printed on an upper surface of the electrode unit with an inductive ink.

7. The wearable device of claim 1, wherein a predetermined potential is applied to the shielding layer so that external static electricity does not flow into the main body unit.

8. The wearable device of claim 1, wherein the electrode unit further includes an electrode pattern layer that is printed on a rear surface of the electrode unit, the electrode pattern layer being in contact with the user's skin through the one or more conductive members and further connected to the shielding layer to cause external static electricity to flow into the user's skin.

9. A wearable device used by being attached to a user's skin, the wearable device comprising:
    a main body unit including a housing and a substrate, the substrate being arranged inside the housing;
    an electrode unit including a sensing electrode connected to the main body unit; and a patch unit including one or more conductive members, the one or more conductive members being configured to electrically connect the electrode unit to the user's skin, wherein the electrode unit includes a conductive shielding layer including an electrode that is connected to a user's skin and not electrically connected to the main body unit.

\* \* \* \* \*